US008193196B2

(12) United States Patent
Viscomi et al.

(10) Patent No.: US 8,193,196 B2
(45) Date of Patent: Jun. 5, 2012

(54) POLYMORPHOUS FORMS OF RIFAXIMIN, PROCESSES FOR THEIR PRODUCTION AND USE THEREOF IN THE MEDICINAL PREPARATIONS

(75) Inventors: Giuseppe Claudio Viscomi, Sasso Marconi (IT); Manuela Campana, Bologna (IT); Donatella Confortini, Calderara di Reno (IT); Maria Miriam Barbanti, Bologna (IT); Dario Braga, Bologna (IT)

(73) Assignee: Alfa Wassermann, S.p.A., Bologna (IT)

( * ) Notice: Subject to any disclaimer, the term of this patent is extended or adjusted under 35 U.S.C. 154(b) by 552 days.

(21) Appl. No.: 11/658,702

(22) PCT Filed: Feb. 27, 2006

(86) PCT No.: PCT/EP2006/001755
§ 371 (c)(1),
(2), (4) Date: Oct. 8, 2007

(87) PCT Pub. No.: WO2006/094662
PCT Pub. Date: Sep. 14, 2006

(65) Prior Publication Data
US 2009/0130201 A1 May 21, 2009

(30) Foreign Application Priority Data
Mar. 3, 2005 (EP) .................................. 05004695

(51) Int. Cl.
*C07D 498/22* (2006.01)
*A61K 31/395* (2006.01)
*A61P 31/04* (2006.01)

(52) U.S. Cl. .................................. 514/254.11; 540/456
(58) Field of Classification Search .................. 540/456; 514/254.11
See application file for complete search history.

(56) References Cited

U.S. PATENT DOCUMENTS
4,341,785 A    7/1982   Marchi et al.

FOREIGN PATENT DOCUMENTS
| | | |
|---|---|---|
| CA | 1215976 | 12/1986 |
| CA | 1218650 | 3/1987 |
| EP | 0 161 534 A2 | 11/1985 |
| EP | 0161534 A2 | 11/1985 |
| EP | 1698630 A1 | 9/2006 |
| EP | 1557421 B1 | 5/2007 |
| IT | MI2005A000345 | 9/2006 |
| WO | WO 2005/044823 A | 5/2005 |

OTHER PUBLICATIONS

Viscomi, G. et al., "Crystal Forms of Rifaximin and Their Effect on Pharmaceutical Properties," CrystEngComm, 2008, 10, 1074-1081.
Italian Product Label for NORMIX (rifaximin), Apr. 23, 1985.
Cellai, L. et al., "A Study of Structure-Activity Relationships in 4-Deoxypyrido[1',2'-1,2] imidazo[5,4-c]rifamycin SV Derivatives by Electron Spectroscopy for Chemical Analysis and 1H NMR," Molecular Pharmacology, 27:103-108, 1984.
European Patent No. 1 557 421, Opposition Proceedings, "Opponent Response to the Late Submissions of Patentee," Jun. 11, 2009.
European Patent No. 1 557 421, Opposition Proceedings, "Patentee Response to Opponent Statement Setting Out the Grounds of Appeal," Jun. 2, 2010.
Zach Systems SPA, "Synthesis of rifaximin obtained according to examples 7 and 9 reported in European Patent EP0161534," May 13, 2010.
European Patent No. 1 557 421, Reply to the Communication pursuant to Article 96(2), May 2, 2006.
European Patent No. 1 557 421, Opposition Proceedings, "Notice of opposition to a European patent," Feb. 11, 2008.
European Patent No. 1 557 421, Opposition Proceedings, Patentee response to Notice of Opposition, Sep. 10, 2008.
European Patent No. 1 557 421, Opposition Proceedings, Opinion of the Opposition Division, Jan. 19, 2009.
European Patent No. 1 557 421, Opposition Proceedings, Patentee response to summons to attend oral proceedings, Apr. 22, 2009.
European Patent No. 1 557 421, Opposition Proceedings, Opponent response to summons to attend oral proceedings, Apr. 29, 2009.
European Patent No. 1 557 421, Opposition Proceedings, Patentee response to brief communication, May 29, 2009.
European Patent No. 1 557 421, Opposition Proceedings, European Patent Office Decision rejecting the opposition, Jul. 8, 2009.
European Patent No. 1 557 421, Opposition Proceedings, Appellant Notice of Appeal, Sep. 18, 2009.
European Patent No. 1 557 421, Opposition Proceedings, Appellant Statement of Grounds for Appeal, Nov. 18, 2009.
Alvisi, V. et al., "Treatment of Secretory Diarrhoeas—A Double-Blind Trial of the Effectiveness of Rifaximin (L 105) and Neomycin," Clinical Trials Journal, 1984, 21, No. 4, pp. 215-223.
Rodriguez-Spong, B. et al., "General Principles of Pharmaceutical Solid Polymorphism: a Supramolecular Perspective," Advanced Drug Delivery Reviews, 56 (2004), 241-274.
Morris, K.R. et al., "Theoretical Approaches to Physical Transformations of Active Pharmaceutical Ingredients During Manufacturing Processes," Advanced Drug Delivery Reviews, 48 (2001), 91-114.
Brufani, M. et al., "X-Ray Crystal Structure of 4-Deoxy-3'-bromopyrido[1',2'-1,2]imidazo[5,4-c]rifamycin S," The Journal of Antibiotics, 37:12, 1623-1627 (Dec. 1984).
Soro, O. et al., "Selection of Rifampicin-Resistant Mycobacterium Tuberculosis Does Not Occur in the Presence of Low Concentrations of Rifaximin," Clin Microbiol Infect, 1997, 3:147-151.

(Continued)

*Primary Examiner* — Bruck Kifle
(74) *Attorney, Agent, or Firm* — Sam K. Tahmassebi; TechLaw, LLP

(57) ABSTRACT

Crystalline polymorphous forms of the rifaximin (INN) antibiotic named rifaximin δ and rifaximin ε useful in the production of medicinal preparations containing rifaximin for oral and topical use and obtained by means of a crystallization process carried out by hot-dissolving the raw rifaximin in ethyl alcohol and by causing the crystallization of the product by addition of water at a determinate temperature and for a determinate period of time, followed by a drying carried out under controlled conditions until reaching a settled water content in the end product, are the object of the invention.

24 Claims, 2 Drawing Sheets

OTHER PUBLICATIONS

TicinumLab. Example 7, Patent EP 0 161 534, "Synthesis of 4-Deoxy-4'methyl-pyrido-[1',2':1,2]imidazo]5,4-c]ryfamicin SV.", (Apr. 2009).

TicinumLab. Example 9, Patent EP 0 161 534, "Synthesis of 4-Deoxy-4'methyl-pyrido-[1',2':1,2]imidazo]5,4-c]ryfamicin SV.", (Apr. 2009).

Department of Health and Human Services, Certificate of GMP Compliance of a Manufacturer, Nov. 16, 2007.

European Medicines Industry, ICH Topic Q6A, Specifications: Test Procedures and Acceptance Criteria for New Drug Substances and New Drug Products: Chemical Substances, pp. 1-32, 2000.

Henwood, S.Q. et al., "Solubility and Dissolution Properties of Generic Rifampicin Raw Materials," Drug Development and Industrial Pharmacy, 26(4), 403-408 (2000).

Morris, K.R. "Polymorphism in Pharmaceutical Solids," in "Structural Aspects of Hydrates and Sovates," H.G. Brittain editor, Drugs and the Pharmaceutical Sciences, vol. 95, Chapter 4, pp. 125-181, 1999.

Rifaximin—Intrinsic Dissolution Experimental Data, Apr. 2009.

Bacchi, A. et al., "Sampling Rifamycin Conformational Variety by Cruising Through Crystal Forms: Implications for Polymorph Screening and for Biological Models," New J. Chem., 2008, 32, 1725-1735.

Venturini, A.P. "Pharmacokinetics of L/105, a New Rifamycin, in Rats and Dogs, after Oral Administration," Chemotherapy 29:1-3 (1983).

Pelizza, G. "Polymorphism of Rifampicin," II Farmaco—Ed. Sc., vol. 32, No. 7, pp. 471-481, 1977.

Rao, R.N. et al., "O-Line 2D-LC-ESI/MS/MS Determination of Rifaximin in Rat Serum," Biomed. Chromatogr. 2009, 1-6.

Descombe, J.J. et al., "Pharmacokinetic Study of Rifaximin After Oral Administration in Healthy Volunteers," Int. J. Clin. Pharm. Res. XIV(2), 51-56 (1994).

POLYMORPHOUS FORMS OF RIFAXIMIN, PROCESSES FOR THEIR PRODUCTION AND USE THEREOF IN THE MEDICINAL PREPARATIONS

CROSS REFERENCE TO RELATED APPLICATION

This application is a 35 USC §371 National Phase Entry Application from PCT/EP2006/001755, filed Feb. 27, 2006, and designating the United States.

BACKGROUND OF THE INVENTION

The rifaximin (INN; see The Merck Index, XIII Ed., 8304) is an antibiotic pertaining to the rifamycin class, exactly it is a pyrido-imidazo rifamycin described and claimed in the Italian Patent IT 1154655, while the European Patent EP 0161534 describes and claims a process for its production starting from the rifamycin o (The Merck Index, XIII Ed., 8301).

Both these patents describe the purification of the rifaximin in a generic way saying that the crystallization can be carried out in suitable solvents or solvent systems and summarily showing in some examples that the product coming from the reaction can be crystallized from the 7:3 mixture of ethyl alcohol/water and can be dried both under atmospheric pressure and under vacuum without saying in any way neither the experimental conditions of crystallization and drying, nor any distinctive crystallographic characteristic of the obtained product.

The presence of different polymorphs had not been just noticed and therefore the experimental conditions described in both patents had been developed with the goal to get a homogeneous product having a suitable purity from the chemical point of view, apart from the crystallographic aspects of the product itself.

It has now be found, unexpectedly, that some polymorphous forms exist whose formation, in addition to the solvent, depends on the conditions of time and temperature at which both the crystallization and the drying are carried out.

These orderly polymorphous forms will be, later on, conventionally identified as rifaximin δ (FIG. 1) and rifaximin ε (FIG. 2) on the basis of their respective specific diffractograms reported in the present application.

The polymorphous forms of the rifaximin have been characterized through the technique of the powder X-ray diffraction.

The identification and characterization of these polymorphous forms and, contemporarily, the definition of the experimental conditions for obtaining them is very important for a compound endowed with pharmacological activity which, like the rifaximin, is marketed as medicinal preparation, both for human and veterinary use. In fact it is known that the polymorphism of a compound that can be used as active principle contained in a medicinal preparation can influence the pharmaco-toxicologic properties of the drug. Different polymorphous forms of an active principle administered as drug under oral or topical form can modify many properties thereof like bioavailability, solubility, stability, colour, compressibility, flowability and workability with consequent modification of the profiles of toxicological safety, clinical effectiveness and productive efficiency.

What above mentioned is confirmed with authority by the fact that the authorities that regulate the grant of the authorization for the admission of the drugs on the market require that the manufacturing methods of the active principles are standardized and controlled in such a way that they give homogeneous and sound results in terms of polymorphism of the production batches (CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

The need of the above-mentioned standardization has further been strengthened just in the field of the rifamycin antibiotics from Henwood S. Q., de Villiers M. M., Liebenberg W. and Lötter A. P., Drug Development and Industrial Pharmacy, 26 (4), 403-408, (2000), who have ascertained that different production batches of the rifampicin (INN) made from different manufacturers differ among them because they show different polymorphous characteristics, and as a consequence they show different profiles of dissolution together with consequent alteration of the respective pharmacological properties.

By applying the processes of crystallization and drying generically disclosed in the previous patents IT 1154655 and EP 0161534 it has been found that under some experimental conditions the poorly crystalline form of the rifaximin is obtained while under other experimental conditions the other crystalline polymorphous forms of the rifaximin are obtained. Moreover it has been found that some parameters, absolutely not disclosed in the above-mentioned patents, like for instance the conditions of preservation and the relative humidity of the ambient, have the surprising effect to determine the form of the polymorph.

The polymorphous forms of the rifaximin object of the present patent application were never seen or hypothesized, while thinking that a sole homogeneous product would always have been obtained whichever method would have been chosen within the range of the described conditions, irrespective of the conditions used for crystallizing, drying and preserving.

It has now been found that the formation of the δ and ε forms depends on the presence of water within the crystallization solvent, on the temperature at which the product is crystallized and on the amount of water present into the product at the end of the drying phase.

The form δ and the form ε of the rifaximin have then been synthesised and they are the object of the invention.

In particular the form δ is characterised by the residual content of water in the dried solid material in the range from 2.5% and 6% (w/w), more preferably from 3% and 4.5%, while the form ε is the result of a polymorphic transition under controlled temperature moving from the form δ.

These results have a remarkable importance as they determine the conditions of industrial manufacturing of some steps of working which could not be considered critical for the determination of the polymorphism of a product, like for instance the maintaining to a crystallized product a quantity of water in a stringent range of values, or the process of drying the final product, in which a form, namely form δ, has to be obtained prior to continuing the drying to obtain the form δ, or the conditions of preservation of the end product, or the characteristics of the container in which the product is preserved.

Rifaximin exerts its broad antibacterial activity in the gastrointestinal tract against localized gastrointestinal bacteria that cause infectious diarrhea including anaerobic strains. It has been reported that rifaximin is characterized by a negligible systemic absorption, due to its chemical and physical characteristics (Descombe J. J. et al. Pharmacokinetic study of rifaximin after oral administration in healthy volunteers. Int J Clin. Pharmacol. Res., 14 (2), 51-56, (1994))

Now we have found that it is possible on the basis of the two identified polymorphic forms of rifaximin to modulate its level of systemic adsorption, and this is part of the present invention, by administering distinct polymorphous forms of rifaximin, namely rifaximin δ and rifaximin ε. It is possible to have a difference in the adsorption of almost 100 folds in the range from 0.001 to 0.3 µg/ml in blood.

The evidenced difference in the bioavailability is important because it can differentiate the pharmacological and toxicological behaviour of the two polymorphous of rifaximins δ and ε.

As a matter of fact, rifaximin ε is negligibly absorbed through the oral route while rifaximin δ shows a mild absorption.

Rifaximin ε is practically not absorbed, might act only through a topical action, including the case of the gastrointestinal tract, with the advantage of very low toxicity.

On the other way, rifaximin δ, which is mildly absorbed, can find an advantageous use against systemic microorganisms, able to hide themselves and to partially elude the action of the topic antibiotics.

In respect of possible adverse events coupled to the therapeutic use of rifaximin of particular relevance is the induction of bacterial resistance to the antibiotics. Generally speaking, it is always possible in the therapeutic practice with antibiotics to induce bacterial resistance to the same or to other antibiotic through selection of resistant strains.

In case of rifaximin, this aspect is particularly relevant, since rifaximin belongs to the rifamycin family, a member of which, the rifampicin, is largely used in tuberculosis therapy. The current short course treatment of tuberculosis is a combination therapy involving four active pharmaceutical ingredients: rifampicin, isoniazid, ethambutol and pyrazinamide and among them rifampicin plays a pivotal role. Therefore, any drug which jeopardized the efficacy of the therapy by selecting for resistance to rifampicin would be harmful. (Kremer L. et al. "Re-emergence of tuberculosis: strategies and treatment", Expert Opin.Investig.Drugs, 11 (2), 153-157, (2002)).

In principle, looking at the structural similarity between rifaximin and rifampicin, it might be possible by using rifaximin to select resistant strains of *M. tuberculosis* and to induce cross-resistance to rifampicin. In order to avoid this negative event it is crucial to have a control of quantity of rifaximin systemically absorbed.

Under this point of view, the difference found in the systemic absorption of the δ and ε forms of the rifaximin is significant, since also at sub-inhibitory concentration of rifaximin, such as in the range of from 0.1 to 1 µg/ml, selection of resistant mutants has been demonstrated to be possible (Marchese A. et al. In vitro activity of rifaximin, metronidazole and vancomycin against clostridium difficile and the rate of selection of spontaneously resistant mutants against representative anaerobic and aerobic bacteria, including ammonia-producing species. Chemotherapy, 46(4), 253-266, (2000)).

According to what above said, the importance of the present invention, which has led to the knowledge of the existence of the above mentioned rifaximin polymorphous forms and to various industrial routes for manufacturing pure single forms having different pharmacological properties, is clearly strengthened.

The above-mentioned δ and ε forms can be advantageously used as pure and homogeneous products in the manufacture of medicinal preparations containing rifaximin.

As already said, the process for manufacturing rifaximin from rifamycin o disclosed and claimed in EP 0161534 is deficient from the point of view of the purification and identification of the product obtained; it shows some limits also from the synthetic point of view as regards, for instance, the very long reaction times, from 16 to 72 hours, very little suitable for an industrial use and moreover because it does not provide for the in situ reduction of the rifaximin oxidized that may be formed within the reaction mixture.

Therefore, a further object of the present invention is an improved process for the industrial manufacturing of the δ and ε forms of the rifaximin, herein claimed as products and usable as defined and homogeneous active principles in the manufacture of the medicinal preparations containing such active principle.

DESCRIPTION OF THE INVENTION

Figure 1:
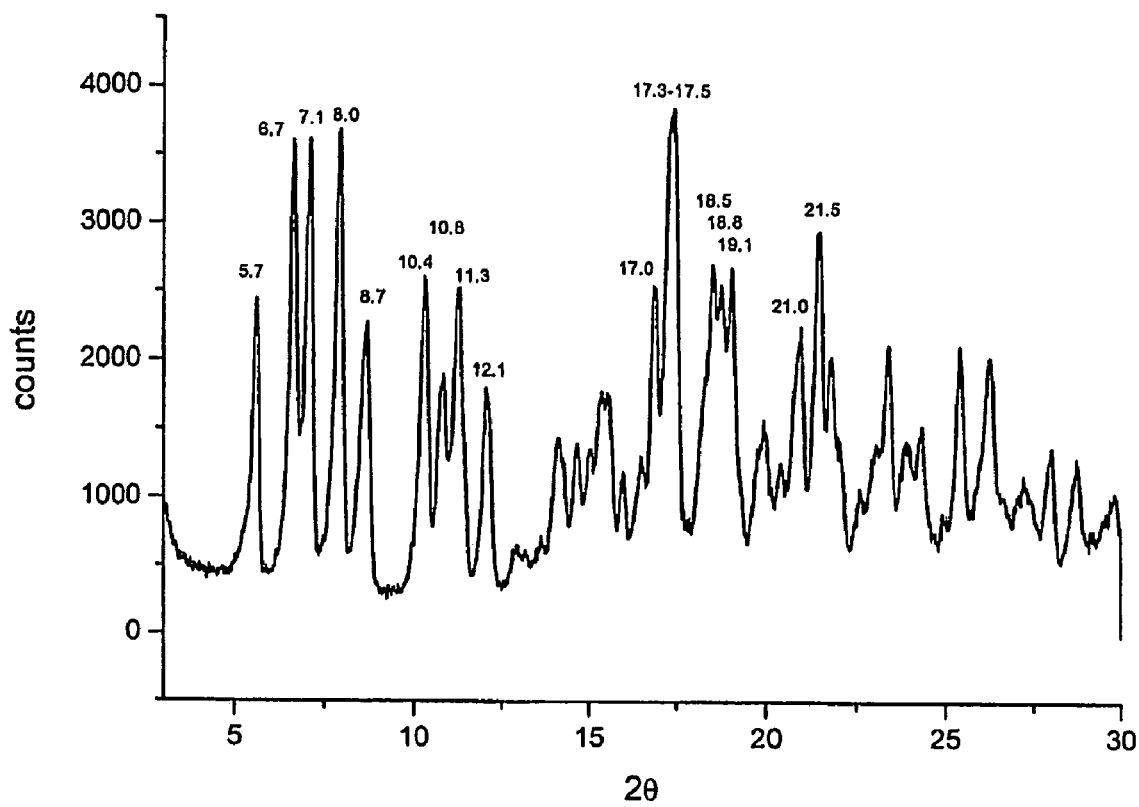
FIG. 1 is a powder X-ray diffractogram of rifaximin δ.

As already said, the form δ and the form ε of the antibiotic known as rifaximin (INN), processes for their production and the use thereof in the manufacture of medicinal preparations for oral or topical route, are object of the present invention.

A process object of the present invention comprises reacting one molar equivalent of rifamycin o with an excess of 2-amino-4-methylpyridine, preferably from 2.0 to 3.5 molar equivalents, in a solvent mixture made of water and ethyl alcohol in volumetric ratios between 1:1 and 2:1, for a period of time between 2 and 8 hours at a temperature between 40° C. and 60° C.

At the end of the reaction the reaction mass is cooled to room temperature and is added with a solution of ascorbic acid in a mixture of water, ethyl alcohol and aqueous concentrated hydrochloric acid, under strong stirring, in order to reduce the small amount of oxidized rifaximin that forms during the reaction and finally the pH is brought to about 2.0 by means of a further addition of concentrated aqueous solution of hydrochloric acid, in order to better remove the excess of 2-amino-4-methylpyridine used in the reaction. The suspension is filtered and the obtained solid is washed with the same solvent mixture water/ethyl alcohol used in the reaction. Such semi finished product is called "raw rifaximin".

The raw rifaximin can be directly submitted to the subsequent step of purification. Alternately, in case long times of preservation of the semi finished product are expected, the raw rifaximin can be dried under vacuum at a temperature lower than 65° C. for a period of time between 6 and 24 hours, such semi finished product is called "dried raw rifaximin".

The so obtained raw rifaximin and/or dried raw rifaximin are purified by dissolving them in ethyl alcohol at a temperature between 45° C. and 65° C. and by crystallizing them by addition of water, preferably in weight amounts between 15% and 70% in respect of the amount by weight of the ethyl alcohol used for the dissolution, and by keeping the obtained suspension at a temperature between 50° C. and 0° C. under stirring during a period of time between 4 and 36 hours.

The suspension is filtered and the obtained solid is washed with water and dried under vacuum or under normal pressure, with or without a drying agent, at a temperature between the room temperature and 105° C. for a period of time between 2 and 72 hours.

The achievement of the δ and ε forms depends on the conditions chosen for the crystallization. In particular, the composition of the solvent mixture from which the crystallization is carried out, the temperature at which the reaction mixture is kept after the crystallization and the period of time at which that temperature is kept, have proven to be critical.

More precisely, the δ and ε rifaximins are obtained when the temperature is first brought to a value between 28° C. and 32° C. in order to cause the beginning of the crystallization, then the suspension is brought to a temperature between 40° C. and 50° C. and kept at this value for a period of time between 6 and 24 hours, then the suspension is quickly cooled to 0° C., in a period of time between 15 minutes and one hour, is filtered, the solid is washed with water and then is dried.

The step of drying has an important part in obtaining the δ and ε polymorphous forms of the rifaximin and has to be checked by means of a suitable method fit for the water dosage, like for instance the Karl Fisher method, in order to check the amount of remaining water present in the product under drying.

The obtaining of the rifaximin δ during the drying in fact depends on the end remaining amount of water which should be comprised from 2.5% (w/w) and 6% (w/w), more preferably between 3% and 4.5%, and not from the experimental conditions of pressure and temperature at which this critical limit of water percent is achieved.

In order to obtain the poorly adsorbed ε form it has to start from the δ form and it has to be continued the drying under vacuum or at atmospheric pressure, at room temperature or at high temperatures, in the presence or in the absence of drying agents, provided that the drying is prolonged for the time necessary so that the conversion in form ε is achieved.

Both the forms δ and ε of the rifaximin are hygroscopic, they absorb water in a reversible way during the time in the presence of suitable conditions of pressure and humidity in the ambient and are susceptible of transformation to other forms.

The transitions from one form to another result to be very important in the ambit of the invention, because they can be an alternative manufacturing method for obtaining the form desired for the production of the medicinal preparations. Therefore, the process that allows to turn the rifaximin δ into rifaximin ε in a valid industrial manner is important part of the invention.

The process concerning the transformation of the rifaximin δ into rifaximin ε comprises drying the rifaximin δ under vacuum or at atmospheric pressure, at room temperature or at high temperatures, in the presence or in the absence of drying agents, and keeping it for a period of time until the conversion is obtained, usually between 6 and 36 hours.

From what above said, it results that during the phase of preservation of the product a particular care has to be taken so that the ambient conditions do not change the water content of the product, by preserving the product in ambient having controlled humidity or in closed containers that do not allow in a significant way the exchange of water with the exterior ambient.

Figure 2:
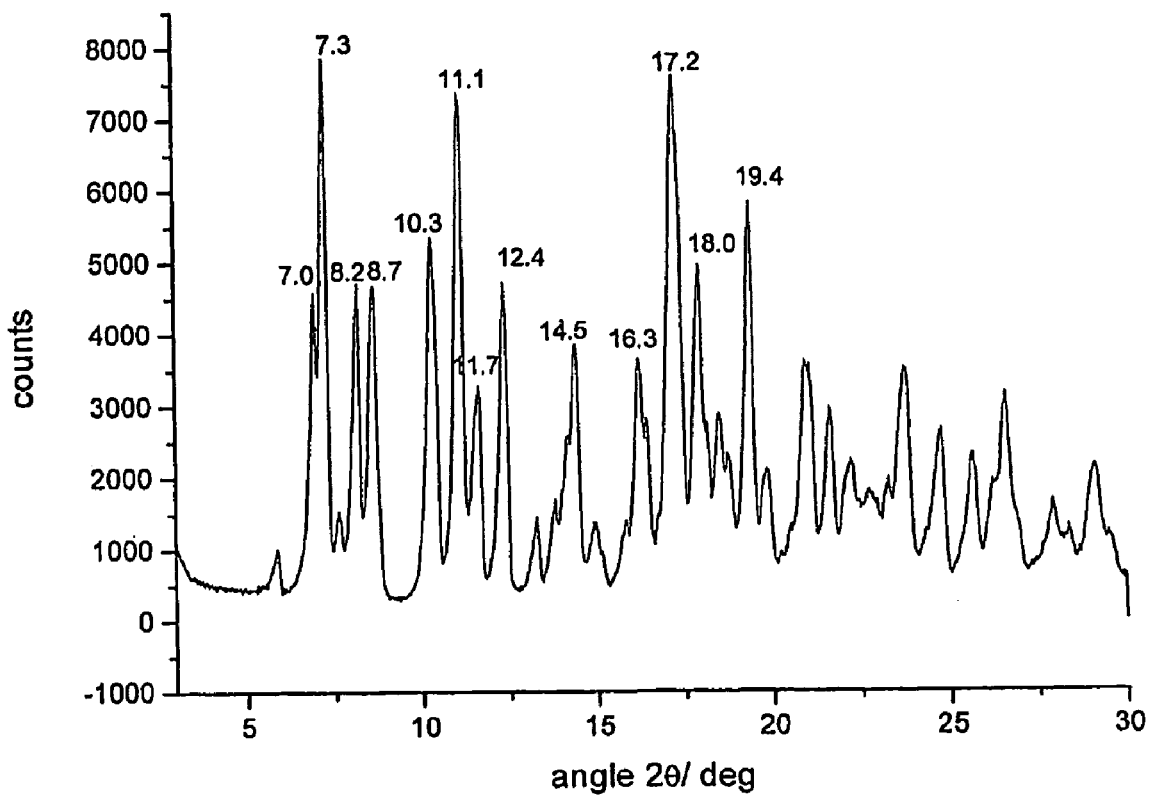
FIG. 2 is a powder X-ray diffractogram of rifaximin ε.

The polymorph called rifaximin δ is characterised from a content of water in the range between 2.5% and 6%, preferably between 3.0% and 4.5% and from a powder X-ray diffractogram (reported in FIG. 1) which shows peaks at the values of the diffraction angles 2θ of 5.70°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The polymorph called rifaximin E is characterized from a powder X-ray diffractogram (reported in FIG. 2) which shows peaks at the values of the diffraction angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

The diffractograms have been carried out by means of the Philips X'Pert instrument endowed with Bragg-Brentano geometry and under the following working conditions:
X-ray tube: Copper
Radiation used: K (α1), K (α2)
Tension and current of the generator: KV 40, mA 40
Monocromator: Graphite
Step size: 0.02
Time per step: 1.25 seconds
Starting and final angular 2θ value: 3.0°÷30.0°

The evaluation of the content of water present in the analysed samples has always been carried out by means of the Karl Fisher method.

Rifaximin δ and rifaximin ε differ each from other also because they show significant differences as regards bioavailability.

A bioavailability study of the two polymorphs has been carried out on Beagle female dogs, treated them by oral route with a dose of 100 mg/kg in capsule of one of the polymorphs, collecting blood samples from the jugular vein of each animal before each dosing and 1, 2, 4, 6, 8 and 24 hours after each dosing, transferring the samples into tubes containing heparin and separating the plasma by centrifugation.

The plasma has been assayed for rifaximin on the validated LC-MS/MS method and the maximum observed plasma concentration (Cmax), the time to reach the Cmax (tmax), and the area under the concentration -time curve (AUC) have been calculated.

The experimental data reported in the following table 1 clearly show that rifaximin ε is negligibly absorbed, while rifaximin δ is absorbed at a value (Cmax=0.308 µg/ml) comprised in the range of from 0.1 to 1.0 µg/ml.

TABLE 1

Pharmacokinetic parameters for rifaximin polimorphs following single oral administration of 100 mg/kg by capsules to female dogs

|  | Cmax ng/ml Mean | Tmax h Mean | AUC0-24 ng · h/ml Mean |
|---|---|---|---|
| Polimorph δ | 308.31 | 2 | 801 |
| Polimorph ε | 6.86 | 4 | 42 |

The above experimental results further point out the differences existing among the two rifaximin polymorphs.

The forms δ and ε can be advantageously used in the production of medicinal preparations having antibiotic activity, containing rifaximin, for both oral and topical use. The medicinal preparations for oral use contain the rifaximin δ and ε together with the usual excipients as diluting agents like mannitol, lactose and sorbitol; binding agents like starchs, gelatines, sugars, cellulose derivatives, natural gums and polyvinylpyrrolidone; lubricating agents like talc, stearates, hydrogenated vegetable oils, polyethylenglycol and colloidal silicon dioxide; disintegrating agents like starchs, celluloses, alginates, gums and reticulated polymers; colouring, flavouring and sweetening agents.

All the solid preparations administrable by oral route can be used in the ambit of the present invention, for instance coated and uncoated tablets, capsules made of soft and hard gelatine, sugar-coated pills, lozenges, wafer sheets, pellets and powders in sealed packets.

The medicinal preparations for topical use contain the rifaximin δ and ε together with the usual excipients like white petrolatum, white wax, lanoline and derivatives thereof, stearylic alcohol, propylenglycol, sodium lauryl sulfate, ethers of the fatty polyoxyethylene alcohols, esters of the fatty polyoxyethylene acids, sorbitan monostearate, glyceryl monostearate, propylene glycol monostearate, polyethylene glycols, methylcellulose, hydroxymethylpropylcellulose, sodium carboxymethylcellulose, colloidal aluminium and magnesium silicate, sodium alginate.

All the topical preparations can be used in the ambit of the present invention, for instance the ointments, the pomades, the creams, the gels and the lotions.

The invention is herein below illustrated from some examples that do not have to be taken as a limitation of the invention: from what described results in fact evident that the forms δ and ε can be obtained by suitably combining between them the above mentioned conditions of crystallization and drying.

EXAMPLE 1

Preparation of Raw Rifaximin and of Dried Raw Rifaximin

In a three-necked flask equipped with mechanic stirrer, thermometer and reflux condenser, 120 ml of demineralised water, 96 ml of ethyl alcohol, 63.5 g of rifamycin o and 27.2 g of 2-amino-4-methylpyridine are loaded in succession at room temperature. After the loading, the mass is heated at 47±3° C., is kept under stirring at this temperature for 5 hours, then is cooled to 20±3° C. and, during 30 minutes, is added with a mixture, prepared separately, made of 9 ml of demineralised water, 12.6 ml of ethyl alcohol, 1.68 g of ascorbic acid and 9.28 g of aqueous concentrated hydrochloric acid. At the end of the addition, the mass is kept under stirring for 30 minutes at an interior temperature of 20±3° C. and then, at the same temperature, 7.72 g of concentrated hydrochloric acid are dripped until a pH equal to 2.0.

At the end of the addition, the mass is kept under stirring, always at an interior temperature equal to 20° C., for 30 minutes, then the precipitate is filtered and washed by means of a mixture made of 32 ml of demineralised water and of 25 ml of ethyl alcohol. The so obtained "raw rifaximin" (89.2 g) is dried under vacuum at room temperature for 12 hours obtaining 64.4 g of "dried raw rifaximin" which shows a water content equal to 5.6%. The product by further drying under vacuum until the weight of 62.2 g of dried raw rifaximin having a water content equal to 3.3%, whose diffractogram corresponds to the polymorphous form δ characterized from a powder X-ray diffractogram showing peaks at values of angles 2θ of 5.7°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The product is hygroscopic.

EXAMPLE 2

Preparation of Rifaximin ε

Example 1 is repeated and after having obtained the δ form, the solid powder is further dried under vacuum for 24 hours at the temperature of 65° C. The product obtained is rifaximin ε characterized from a powder X-ray diffractogram showing peaks at values of angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

EXAMPLE 3

Bioavailability in Dogs By Oral Route

Eight pure-bred Beagle females dogs having 20 weeks of age and weighing between 5.0 and 7.5 kg have been divided into two groups of four.

The first of these group has been treated with rifaximin δ, the second with rifaximin ε according to the following procedure.

To each dog have been administered by the oral route 100 mg/kg of one of the rifaximin polymorphs into gelatine capsules and blood samples of 2 ml each have been collected from the jugular vein of each animal before each dispensing and 1, 2, 4, 6, 8 and 24 hours after the administration.

Each sample has been transferred into a tube containing heparin as anticoagulant and has been centrifuged; the plasma has been divided into two aliquots, each of 500 μl, and has been frozen at −20° C.

The rifaximin contained in the plasma has been assayed by means of the validated LC-MS/MS method and the following parameters have been calculated according to standard non-compartmental analysis:

Cmax=maximum observed plasma concentration of rifaximin in the plasma;

Tmax=time at which the Cmax is reached;

AUC=area under the concentration-time curve calculated through the linear trapezoidal rule.

The results reported in the table 1 clearly show how the rifaximin δ is much more absorbed, more than 40 times, in respect of rifaximin ε, which is practically not absorbed.

The invention claimed is:

1. A process for the production of the rifaximin polymorphic forms δ and ε, wherein:
   reacting a molar equivalent of rifamycin o with an excess of 2-amino-4-methylpyridine in a first solvent mixture, comprising water and ethyl alcohol in volumetric ratios between 1:1 and 2:1, for between 2 and 8 hours at a temperature between 40° C. and 60° C., to obtain a first reaction mixture;
   treating the first reaction mixture at room temperature with a solution of ascorbic acid in a mixture of water, ethyl alcohol and concentrated aqueous hydrochloric acid to obtain a second reaction mixture;
   adding concentrated aqueous solution of hydrochloric acid to the second reaction mixture to bring the pH to 2.0 thereby obtaining a first suspension;
   filtering the first suspension to obtain a first solid;
   washing the first solid with the first solvent mixture to obtain raw rifaximin;
   dissolving the raw rifaximin in ethyl alcohol at a temperature between 45° C. and 65° C.;
   forming a precipitate by adding water and lowering the temperature of the mixture to between 50° C. and 0° C. while stirring for between 4 and 36 hours to obtain a second suspension;
   filtering the second suspension to obtain a second solid;
   washing the second solid with water and drying it under vacuum or under normal pressure, with or without a drying agent, at a temperature between room temperature and 105° C., for between 2 and 72 hours,
   wherein the rifaximin polymorphic form δ is free from other polymorphic forms of rifaximin and has x-ray powder diffraction pattern peaks at about 5.7°±0.2, 10.8°±0.2, 12.1°±0.2, and 17.0°±0.2 2-θ, and wherein the rifaximin polymorphic form ε is free from other polymorphic forms of rifaximin and has x-ray powder diffraction pattern peaks at about 8.2°±0.2, 12.4°±0.2, and 16.3°±0.2 2-θ.

2. The process of claim 1, wherein the excess of 2-amino-4-methylpyridine is present at from 2.0 to 3.5 molar equivalents compared to the rifamycin O.

3. The process of claim 1, wherein the amount of water added to form the precipitate is between 15% and 70% by weight compared to the weight of ethyl alcohol used for the dissolution in the previous step.

4. The process of claim 1, wherein when the water is added to form the precipitate, the temperature is lowered to between 28° C. and 32° C.

5. The process of claim 4, further comprising:
stirring the second suspension at between 40° C. and 50° C. for between 6 and 24 hours followed by cooling the mixture to 0° C. for between 15 minutes and one hour to obtain a third suspension; and
filtering the third suspension and drying the obtained solid to a water content of between 2.5% and 6% (w/w).

6. The process of claim 5, wherein the water content is between 3.0% and 4.5%.

7. A solid pharmaceutical composition comprising a therapeutically effective amount of rifaximin δ, rifaximin ε, or a combination thereof, and a pharmaceutically acceptable excipient, together disposed in a formulation for oral administration,
wherein the rifaximin δ has x-ray powder diffraction pattern peaks at about 5.7°±0.2, 10.8°±0.2, 12.1°±0.2, and 17.0°±0.2, 2-θ, and
wherein the rifaximin ε has x-ray powder diffraction pattern peaks at about 8.2°±0.2, 12.4°±0.2, and 16.3°±0.2 2-θ.

8. The pharmaceutical composition of claim 7, wherein the excipient is selected from the group consisting of diluting, binding, lubricating, disintegrating, coloring, flavoring, and sweetening agents.

9. The pharmaceutical composition of claim 7, wherein the formulation for oral administration is selected from the group consisting of coated or uncoated tablet, hard or soft gelatin capsule, sugar-coated pill, lozenge, wafer sheet, pellet, and powder in sealed packet.

10. A solid pharmaceutical composition comprising a therapeutically effective amount of rifaximin δ rifaximin ε, or a combination thereof, in a formulation for topical administration,
wherein the rifaximin δ has x-ray powder diffraction pattern peaks at about 5.7°±0.2, 10.8°±0.2, 12.1°±0.2, and 17.0°±0.2, 2-θ, and
wherein the rifaximin ε has x-ray powder diffraction pattern peaks at about 8.2°±0.2, 12.4°±0.2, and 16.3°±0.2 22-θ.

11. The pharmaceutical composition of claim 10, wherein the formulation for topical administration is selected from the group consisting of ointment, pomade, cream, gel, and lotion.

12. A method of treating bacterial activity in the gastrointestinal tract of a subject, the method comprising:
identifying the needed systemic level of rifaximin; and
administering to the subject a pharmaceutical composition comprising a therapeutically effective amount of rifaximin δ, rifaximin ε, or a combination thereof, thereby reducing the bacterial activity in the gastrointestinal tract,
wherein the rifaximin δ has x-ray powder diffraction pattern peaks at about 5.7°±0.2, 10.8°±0.2, 12.1°±0.2, and 17.0°±0.2, 2-θ, and
wherein the rifaximin δ has x-ray powder diffraction pattern peaks at about 8.2°±0.2, 12.4°±0.2, and 16.3°±0.2, 2-θ.

13. The method of claim 12, wherein the bacterial activity causes infectious diarrhea.

14. The method of claim 12, wherein the bacteria are anaerobic bacteria.

15. The method of ctaim 12, wherein the pharmaceutical composition is administered orally.

16. The method of claim 12, wherein the bacteria are gastrointestinal bacteria.

17. Rifaximin in polymorphic form δ free from other polymorphic forms of rifaximin not derived from form δ by moisture absorption or release, wherein the rifaximin form δ has x-ray powder diffraction pattern peaks at about 5.7°±0.2, 10.8°±0.2, 12.1°±0.2, and 17.0°±0.2 2-θ.

18. The rifaximin of claim 17, wherein the x-ray powder diffraction pattern further comprises a peak at about 11.3°±0.2 2-θ.

19. The rifaximin of claim 17, wherein the x-ray powder diffraction pattern further comprises peaks at about 7.1°±0.2 and 21.5°±0.2 2-θ.

20. The rifaximin of claim 17, wherein the x-ray powder diffraction pattern further comprises peaks at about 6.7°±0.2 and 8.7°±0.2 2-θ.

21. The rifaximin of claim 17, wherein the polymorph has x-ray powder diffraction pattern peaks at about 5.7°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0° and 21.5°±0.2 2-θ.

22. The rifaximin of claim 17, wherein the polymorph δ has a water content of between 3% and 4.5%.

23. Rifaximin in polymorphic form ε free from other polymorphic forms of rifaximin not derived from form ε by moisture absorption or release, wherein the rifaximin form δ has x-ray powder diffraction pattern peaks at about 8.2°±0.2, 12.4°±0.2, and 16.3°±0.2 2-θ.

24. The rifaximin of claim 17, wherein the polymorph δ has a water content of between 2.5% and 6%.

* * * * *

UNITED STATES PATENT AND TRADEMARK OFFICE
CERTIFICATE OF CORRECTION

| | | |
|---|---|---|
| PATENT NO. | : 8,193,196 B2 | |
| APPLICATION NO. | : 11/658702 | |
| DATED | : June 5, 2012 | |
| INVENTOR(S) | : Giuseppe Claudio Viscomi et al. | |

It is certified that error appears in the above-identified patent and that said Letters Patent is hereby corrected as shown below:

In the Claims:

In column 10, claim 23, line 49, replace "$\delta$" with --$\epsilon$--.

Signed and Sealed this
Thirty-first Day of July, 2012

David J. Kappos
*Director of the United States Patent and Trademark Office*

UNITED STATES PATENT AND TRADEMARK OFFICE
CERTIFICATE OF CORRECTION

PATENT NO. : 8,193,196 B2
APPLICATION NO. : 11/658702
DATED : June 5, 2012
INVENTOR(S) : Giuseppe Claudio Viscomi et al.

It is certified that error appears in the above-identified patent and that said Letters Patent is hereby corrected as shown below:

In the Claims

Column 10, Claim 12, Line 15, replace "$\delta$" with --$\varepsilon$--.

Signed and Sealed this
Twenty-second Day of October, 2024

Katherine Kelly Vidal
*Director of the United States Patent and Trademark Office*